US006129761A

United States Patent [19]
Hubbell

[11] Patent Number: 6,129,761
[45] Date of Patent: *Oct. 10, 2000

[54] INJECTABLE HYDROGEL COMPOSITIONS

[75] Inventor: Jeffrey A. Hubbell, San Marino, Calif.

[73] Assignee: Reprogenesis, Inc., Charlotte, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/478,690

[22] Filed: Jun. 7, 1995

[51] Int. Cl.$^7$ .................................. A61F 2/02; C12N 5/08
[52] U.S. Cl. ........................... 623/11; 424/93.7; 424/426; 623/66
[58] Field of Search ................................ 623/4, 8, 11, 12, 623/16, 66, 901, 93.7; 424/423, 426, 485, 548, 549

[56] References Cited

U.S. PATENT DOCUMENTS

| | | | |
|---|---|---|---|
| 1,995,970 | 3/1935 | Dorough | 260/2 |
| 2,609,347 | 9/1952 | Wilson | 260/2.5 |
| 2,653,917 | 9/1953 | Hammon | 260/2.5 |
| 2,659,935 | 11/1953 | Hammon | 18/55 |
| 2,664,366 | 12/1953 | Wilson | 117/138.8 |
| 2,664,367 | 12/1953 | Wilson | 117/138.8 |
| 2,676,945 | 4/1954 | Higgins | 260/45.7 |
| 2,683,136 | 7/1954 | Higgins | 260/78.3 |
| 2,703,316 | 3/1955 | Schneider | 260/78.3 |
| 2,758,987 | 8/1956 | Salzberg | 260/78.3 |
| 2,846,407 | 8/1958 | Wilson | 260/2.5 |
| 2,951,828 | 9/1960 | Zeile et al. | 260/77.5 |
| 3,531,561 | 9/1970 | Trehu | 264/210 |
| 3,826,241 | 7/1974 | Bucalo | 128/1 R |
| 3,880,991 | 4/1975 | Yolles | 424/22 |
| 3,883,393 | 5/1975 | Knazek et al. | 195/1.8 |
| 3,902,497 | 9/1975 | Casey | 128/296 |
| 3,935,065 | 1/1976 | Doerig | 195/1.7 |
| 3,949,073 | 4/1976 | Daniels et al. | 424/177 |
| 3,960,150 | 6/1976 | Hussain et al. | 128/260 |
| 3,974,526 | 8/1976 | Dardik et al. | 3/1.4 |
| 3,992,725 | 11/1976 | Homsy | 3/1 |
| 3,995,444 | 12/1976 | Clark et al. | 62/306 |
| 4,021,382 | 5/1977 | Stoy et al. | 623/4 |
| 4,026,304 | 5/1977 | Levy | 128/419 |
| 4,060,081 | 11/1977 | Yannas et al. | 128/156 |
| 4,069,307 | 1/1978 | Higuchi et al. | 424/22 |
| 4,137,921 | 2/1979 | Okuzumi | 128/335.5 |
| 4,141,087 | 2/1979 | Shalaby et al. | 3/1 |
| 4,144,126 | 3/1979 | Burbidge | 195/1.1 |
| 4,186,448 | 2/1980 | Brekke | 3/1.9 |
| 4,192,827 | 3/1980 | Mueller et al. | 525/123 |
| 4,206,399 | 6/1980 | Shalaby et al. | 3/1 |
| 4,228,243 | 10/1980 | Iizuka | 435/285 |
| 4,239,664 | 12/1980 | Teag et al. | 260/17.4 |
| 4,243,775 | 1/1981 | Rosensaft et al. | 525/415 |
| 4,277,582 | 7/1981 | Mueller et al. | 525/421 |
| 4,280,954 | 7/1981 | Yannes et al. | 260/123.7 |
| 4,304,591 | 12/1981 | Mueller et al. | 71/93 |
| 4,304,866 | 12/1981 | Green et al. | 435/240 |
| 4,328,204 | 5/1982 | Wasseman et al. | 424/19 |

(List continued on next page.)

FOREIGN PATENT DOCUMENTS

| | | |
|---|---|---|
| 24246/88 | 2/1988 | Australia . |
| 0 153 896 | 9/1985 | European Pat. Off. . |
| 0 248 246 | 6/1986 | European Pat. Off. . |
| 0 248 247 | 6/1986 | European Pat. Off. . |
| 0 226 061 | 6/1987 | European Pat. Off. . |
| 0 282 746 | 9/1988 | European Pat. Off. . |
| 0 339 607 | 11/1989 | European Pat. Off. . |
| 28 53 614 | 7/1979 | Germany . |
| 35 18 150 | 10/1986 | Germany . |
| 4103876 | 8/1991 | Germany . |
| 62 011 459 | 1/1987 | Japan . |
| 63 074 498 | 4/1988 | Japan . |
| 63 196 273 | 8/1988 | Japan . |
| 63 196 595 | 8/1988 | Japan . |
| WO 87/06120 | 10/1987 | WIPO . |
| WO 88/03785 | 6/1988 | WIPO . |
| WO 89/00413 | 1/1989 | WIPO . |
| WO 89/07944 | 9/1989 | WIPO . |
| WO 90/12603 | 11/1990 | WIPO . |
| WO 90/12604 | 11/1990 | WIPO . |
| WO 92/07525 | 5/1992 | WIPO . |
| WO 93/07913 | 4/1993 | WIPO . |
| WO 93/08850 | 5/1993 | WIPO . |
| WO 93/17669 | 9/1993 | WIPO . |
| WO 94/21299 | 9/1994 | WIPO . |
| WO 94/25079 | 11/1994 | WIPO . |
| WO 94/25080 | 11/1994 | WIPO . |

OTHER PUBLICATIONS

Atala, et al., "Endoscopic Treatment Of Vesicoureteral Reflux With A Selfdetachable Balloon System", *J. Urol.*, 148:724–727 (1992).

Atala, et al., "Laparoscopic Correction Of Vesicoureteral Reflux", *J. Urol.*, 150:748–751 (1993).

Buckley, et al., "Endoscopic Correction Of Vesicoureteric Reflux With Injectable Silicone Microparticles" *J. Urol.*, 149:259A (1993).

Claes, et al., "Pulmonary Migration Following Periurethral Polyetrafluoroethylene Injection For Urinary Incontinence", *J. Urol.*, 142:821 (1989).

Hubbell, "Biomaterials In Tissue Engineering", *Bio/Technology*, 13:565–576 (1995).

(List continued on next page.)

*Primary Examiner*—Mickey Yu
*Assistant Examiner*—Dinh X. Nguyen
*Attorney, Agent, or Firm*—Baker & Botts LLP

[57] ABSTRACT

Slowly polymerizing hydrogels are provided which are useful as a means of delivering large numbers of isolated cells via injection. The gels promote engraftment and provide three dimensional templates for new cell growth. The resulting tissue is similar in composition and histology to naturally occurring tissue. This method can be used for a variety of reconstructive procedures, including custom molding of cell implants to reconstruct three dimensional tissue defects, as well as implantation of tissues generally. The polymers permit construction of muscle and cartilage tissues which are useful to repair defects such as reflux and incontinence.

17 Claims, No Drawings

U.S. PATENT DOCUMENTS

| | | | |
|---|---|---|---|
| 4,347,847 | 9/1982 | Usher | 128/334 |
| 4,348,329 | 9/1982 | Chapman | 260/403 |
| 4,352,883 | 10/1982 | Lim | 435/178 |
| 4,356,261 | 10/1982 | Kuettner | 435/68 |
| 4,391,797 | 7/1983 | Folkman et al. | 424/19 |
| 4,416,986 | 11/1983 | Markus et al. | 435/68 |
| 4,427,808 | 1/1984 | Stol et al. | 524/24 |
| 4,431,428 | 2/1984 | Schmer | 604/897 |
| 4,438,198 | 3/1984 | Schmer | 435/178 |
| 4,439,152 | 3/1984 | Small | 433/173 |
| 4,440,921 | 4/1984 | Allcock et al. | 528/168 |
| 4,444,887 | 4/1984 | Hoffmann | 435/240 |
| 4,446,229 | 5/1984 | Indech | 435/1 |
| 4,446,234 | 5/1984 | Russo et al. | 435/29 |
| 4,450,150 | 5/1984 | Sidman | 424/1.1 |
| 4,456,687 | 6/1984 | Green | 435/241 |
| 4,458,678 | 7/1984 | Yannas et al. | 128/155 |
| 4,485,096 | 11/1984 | Bell | 424/95 |
| 4,485,097 | 11/1984 | Bell | 424/95 |
| 4,489,056 | 12/1984 | Himmelstein et al. | 424/22 |
| 4,494,385 | 1/1985 | Kuraoka et al. | 62/306 |
| 4,495,174 | 1/1985 | Allcock et al. | 424/78 |
| 4,505,266 | 3/1985 | Yannas et al. | 128/1 |
| 4,520,821 | 6/1985 | Schmidt et al. | 128/334 |
| 4,528,265 | 7/1985 | Becker | 435/172.1 |
| 4,544,516 | 10/1985 | Hughes et al. | 264/108 |
| 4,545,082 | 10/1985 | Hood | 623/1 |
| 4,546,500 | 10/1985 | Bell | 623/1 |
| 4,553,272 | 11/1985 | Mears | 623/1 |
| 4,559,298 | 12/1985 | Fahy | 435/1 |
| 4,559,304 | 12/1985 | Kasai et al. | 435/240 |
| 4,563,350 | 1/1986 | Nathan et al. | 424/95 |
| 4,563,490 | 1/1986 | Stol et al. | 524/24 |
| 4,576,608 | 3/1986 | Homsy | 623/11 |
| 4,595,713 | 6/1986 | St. John | 523/105 |
| 4,609,551 | 9/1986 | Caplan et al. | 424/95 |
| 4,627,853 | 12/1986 | Campbell et al. | 623/16 |
| 4,637,931 | 1/1987 | Schmitz | 424/73 |
| 4,642,120 | 2/1987 | Nevo et al. | 623/16 |
| 4,645,669 | 2/1987 | Reid | 424/95 |
| 4,675,189 | 6/1987 | Kent et al. | 424/490 |
| 4,675,284 | 6/1987 | Leevy et al. | 435/6 |
| 4,681,763 | 7/1987 | Nathanson et al. | 424/95 |
| 4,689,293 | 8/1987 | Goosen et al. | 435/1 |
| 4,713,070 | 12/1987 | Mano | 623/1 |
| 4,721,096 | 1/1988 | Naughton et al. | 128/1 |
| 4,734,373 | 3/1988 | Bartal | 435/296 |
| 4,757,017 | 7/1988 | Cheung | 435/240.23 |
| 4,757,128 | 7/1988 | Domb et al. | 528/271 |
| 4,778,749 | 10/1988 | Vasington et al. | 435/2 |
| 4,808,353 | 2/1989 | Nambu et al. | 623/66 |
| 4,846,836 | 7/1989 | Grande | 623/11 |
| 4,853,324 | 8/1989 | Viles et al. | 435/2 |
| 4,868,121 | 9/1989 | Scharp et al. | 435/268 |
| 4,880,622 | 11/1989 | Allcock et al. | 424/78 |
| 4,891,225 | 1/1990 | Langer et al. | 424/428 |
| 4,902,295 | 2/1990 | Walthall et al. | 623/12 |
| 4,946,938 | 8/1990 | Magill et al. | 528/399 |
| 4,963,489 | 10/1990 | Naughton et al. | 435/240.1 |
| 4,988,761 | 1/1991 | Ikada et al. | 524/557 |
| 5,032,508 | 7/1991 | Naughton et al. | 435/32 |
| 5,041,138 | 8/1991 | Vacanti et al. | 623/16 |
| 5,089,606 | 2/1992 | Cole et al. | 536/54 |
| 5,144,016 | 9/1992 | Skjak-Braek et al. | 536/3 |
| 5,213,580 | 5/1993 | Slepian et al. | 623/1 |
| 5,277,915 | 1/1994 | Provonchee et al. | 424/485 |
| 5,336,263 | 8/1994 | Ersek et al. | 623/11 |
| 5,516,532 | 5/1996 | Atala et al. | 623/11 |
| 5,575,815 | 11/1996 | Slepian et al. | 623/11 |
| 5,634,946 | 6/1997 | Slepian | 623/11 |
| 5,662,609 | 9/1997 | Slepian | 604/101 |
| 5,709,854 | 1/1998 | Griffith-Cima et al. | 424/93.7 |
| 5,749,915 | 5/1998 | Slepian | 623/1 |
| 5,749,922 | 5/1998 | Slepian et al. | 623/1 |
| 5,843,156 | 12/1998 | Slepian et al. | 623/1 |

OTHER PUBLICATIONS

Leonard, et al., "Endoscopic Injection Of Glutaraldehyde Cross–Linked Bovine Dermal Collagen For Correction Of Vesicoureteral Reflux", *J. Urol.*, 145:115 (1991).

Malizia, et al., "Migration And Granulomatous Reaction After Periurethral Injection Of Polymer (Polytetrafluoroethylene", *JAMA*, 251:3277 (1984).

March, "Advanced Organic Chemistry", Wiley–Interscience Publication, 4th Edition. (1992).

Henly, et al., "Particulate Silicone For Use In Periurethral Injections: A Study Of Local Tissue Effects And A Search For Migration", *J. Urol.*, 147:376A (1992).

Allcock, H. R., et al., "Phosphonitrilic Compounds. IV. High Molecular Weight Poly[bis(amino)phosphazenes] and Mixed–Substituent Poly(aminophosphazenes)," *Inorg. Chem.* 11(11):2584–2590 (1972).

Allcock, H. R., et al., "Polyphosphazenes with Etheric Side Groups: Prospective Biomedical and Solid Electrolyte Polymers," *Macromolecules* 19:1508–1512 (1986).

Allcock & Kwon, "Glyceryl Phosphazenes: Synthesis, Properties, and Hydrolysis," *Macromolecules* 21(7):1980–1985 (1988).

Allcock & Scopelianos, "Synthesis of Sugar–Substituted Cyclic and Polymeric Phosphazenes and Their Oxidation, Reduction, and Acetylation Reactions," *Macromolecules* 16(5)715–719 (1983).

Anderson, Kathryn D., et al., "Gene Expression in Implanted Rat Hepatocytes Following Retroviral–Mediated Gene Transfer," *Somatic Cell & Mol. Gen.*, 15(3):215–227 (1989).

Atala, A., et al., "Endoscopic Treatment of Vesicoureteral Reflux with a Chondrocyte–Alginate Suspension", *The Journal of Urology* 152:641–643 (Aug., 1994).

Atala, A., et al., "Injectable Alginate Seeded with Chondrocytes as a Potential Treatment for Vesicoureteral Reflux," *The Journal of Urology* 150:745–747 (Aug., 1993).

Atala, A., et al., "Sonography with Sonicated Albumin in the Detection of Vesidoureteral Reflux," *The Journal of Urology* 150:756–758 (Aug., 1993).

Baklund, Erik–olof, et al. "Toward a Transplantation Therapy in Parkinson's Disease," *Annals of the N.Y. Acad. of Sci.* 495:658–673 (1987).

Ben–Ze'ev, Avri, et al. "Cell–Cell and Cell–Matrix Interactions Differentially Regulate the Expression of Hepatic and Cytoskeletal Genes in Primary Cultures of Rat Hepatocytes," *Proc. Natl. Acad. Sci. USA* 85:2161–2165 (Apr. 1988).

Bennett & Hirt, "A History of Tissue Expansion," *Dermatol. Surg. Oncol.* 19:1066–1073 (1993).

Biers, Elizabeth, "Organogenesis' Human Artery Equivalent May Revolutionize Vascular Grafts," *Genetic Engineering News* (Nov./Dec. 1987).

"Brain Graft Seeks to Relieve Huntington Disease Patient," *New York Times* (Mar. 4, 1988).

Breuer, C., et al., "Tissue Engineering Heart Valves," American Chemical Society Spring Meeting, (Apr. 2–6, 1995).

Brown, Norman, "Fibrin–Collagen Nerve Repair Device," Inventors: Russ Griffiths, Larry Stensaas & Ken Horch, Letter dated May 10, 1988.

Cao, Y, et al., "Bone Reconstruction with Tissue Engineered Vascularized Bone," (Abstract) Apr. 30–May 3, 1995.

Cao, Y., et al., "The Generation of Neo–Tendon Using Synthetic Polymers seeded with Tenocytes," *Transplantation Proceedings*, 26(6):3390–3392 (1994).

Chaikin, Andrew, "Tissue Engineering: Science Non–Fiction," *Medical Industry Executive* pp 6–7 (May, 1993).

Chuang, Vincent P., et al., "Sheath Needle for Liver Biopsy in High–Risk Patients," *RSNA* pp 261–262 (1988).

Cilento, Bartley, et al., "Phenotypic and Cytogenetic Characterization of Human Bladder Urothelia Expanded in Vitro," *Microbiology & Immunology* 152:665–670 (Aug., 1994).

Cohen, Bernard H., "Navigating Through Tissue Expansion Terminology," *J. Dermatol. Surg. Oncol.* 19:614–615 (1993).

Cosimi, et al., "Transplantation of Skin," *Surgical Clinics of N.A.* 58(2), 435–451 (Apr., 1978).

da Silva, C.F., "An In Vivo Model to Quantify Motor and Sensory Peripheral Nerve Regeneration Using Bioresorbable Nerve Guide Tubes," *Brain Research*, 342:307–315 (1985).

del Cerro, M., et al., "Retinal Transplants into One Anterior Chamber of the Rat Eye," *Neuroscience* 21:(3)707–23 (Jun. 1987).

Doillon, C. J., et al., "Collagen–Based Wound Dressings: Control of the Pore Structure and Morphology," *Journal of Biomedical Materials Research*, 20:1219–1228 (1986).

Doillon, C. J., et al., "Epidermal Cells Cultured on a Collagen–Based Material," G.W. Bailey, Editor, Proceedings of the 44th Annual Meeting of the Electron Microscopy Society of America, (1986).

Ebata, et al. "Liver Regeneration Utilizing Isolated Hepatocytes Transplanted into the Rat Spleen," *Surg. Forum* 29:338–340 (1978).

Ferro, M. A., et al., "Periurethral Granuloma: Unusual Complication of Teflon Periurethral Injection," *Urology* 31(5):422–423 (May, 1988).

Folkman, Judah, et al., "Angiogenic Factors," *Science* 235:442–447 (Jan. 23, 1987).

Fontaine, H., et al., "Optimization Studies on Retroviral Mediated Gene Transfer into Rat Hepatocytes: Implications for Gene Therapy," The Society of University Surgeons, Resident's Program, Cincinnati, Ohio (Feb. 15, 1992).

Freshney, "The Culture Environment: I. Substrate, Gas Phase, and Temperature," *Culture of Animal Cells* pp55–56 (Alan R. Liss, NY 1983).

Gilbert, James C., et al., "Cell Transplantation of Genetically Altered Cells on Biodegradable Polymer Scaffolds in Syngeneic Rats," Department of Surgery, The Children's Hospital and Harvard Medical School, Boston, Massachusetts.

Grolleman, C. W. J., et al., "Studies on a Bioerodible Drug Carrier System Based on Polyphosphazene," *Journal of Controlled Release* 3:143–154 (1986).

Hammond, Dennis C., et al., "Morphologic Analysis of Tissue–Expander Shape Using a Biomechanical Model," *Plastic and Reconstructive Surgery* 92(2):255–259 (Aug., 1993).

Harris, A. K., et al. "Silicone Rubber Substrata: A New Wrinkle in the Study of Cell Locomotion," *Science* 208:177–179 (1980).

Ingber, Donald E., et al., "Endothelial Growth Factors and Extracellular Matrix Regulate DNA Synthesis Through Modulation of Cell and Nuclear Expansion," *In Vitro Cellular and Developmental Biology* 23(5):387–394 (May, 1987).

Ingber, Growth Control Through Fibronectin–Dependent Modulation of Cell Shape.: *J. Cell Biol.* 105:219a (1987).

Jones, Peter A., "Degradation of Artificial Tissue Substrates," *Cancer Invasion and Metastesis: Biologic and Therapeutic Aspects*, 177–185 (Raven Press, NY 1984).

Kenna, Denis M., et al., "Diffusion of Antibiotics Across Tissue Expanders: An in Vitro Study," *Annals of Plastic Surgery* 32(4):346–349 (Apr., 1994).

Klagsbrun, Michael, "Large–Scale Preparation of Chondrocytes," *Methods in Enzymology* vol. LVIII, Academic Press, New York, 1979.

Klompmaker, J., et al, "Porous Polymer Implants for Repair of Full–Thickness Defects of Articular Cartilage: An Experimental Study in Rabbit and Dog," *Biomaterials* 13(9):625–634 (1992).

Kolata, Gina, "Parkinson Procedure: Fervor Turns to Disillusion," *The New York Times*, (Apr. 21, 1988).

Langer & Moses, "Biocompatible Controlled Release Polymers for Delivery of Polypeptides and Growth Factors," *Journal of Cellular Biochemistry*, 45:340–345 (1991).

Langer and Vacanti, "Tissue Engineering," *Science* 260:920–926 (May 14, 1993).

Leong, K. W., et al., "Bioerodible Polyanhydrides as Drug–Carrier Matrices. I: Characterization, Degradation, and Release Characteristics," *Journal of Biomedical Materials Research*, 19:941–955 (1985).

Lewin, "Disappointing Brain Graft Results," *Science*, p. 1407 (Jun. 10, 1988).

Macklis, J. D., et al., "Cross–Linked Collagen Surface for Cell Culture that is Stable, Uniform, and Optically Superior to Conventional Surfaces," *In Vitro Cellular & Developmental Biology*, 21(3)(1): 189–194 (Mar. 1985).

Marciano and Gash, "Structural and Functional Relationships of Grafted Vasopressin Neurons," *Brain Res.*, 370(2):338–342 (Apr. 9, 1986).

Millaruelo, A. I., "Role of Plasminogen Activator and its Inhibitors in Axonal Outgrowth and Regeneration In Vivo," *Caltech Biology*, (1987).

Mittleman & Marraccini, "Pulmonary Teflon Granulomas Following Periurethral Teflon Injection for Urinary Incontinence," *Arch. Pathol. Lab. Med.* 107:611–612 (Nov. 1983).

Mooney, D., "Control of Hepatocyte Function Through Polymer–Substrate Modulation," *Thesis Proposal—Department of Chemical Enineering, Massachusetts Institute of Technology* (Sep. 22, 1989).

Mooney, D., "Switching from Differentiation to Growth in Hepatocytes: Control by Extracellular Matrix," *J. Cell. Phys.* (151):497–505 (1992).

Mooney, D., et al., "Integrating Cell Transplantation and Controlled Drug Delivery Technologies to Engineer Liver Tissue," (abstract) Materials Research Society, (Apr. 17–21, 1995).

Nastelin, J. G., "Pancreatic Islet Cell Transplantation: Optimization of Islet Cell Adhesion by Altering Polymer Surface Characteristics," Harvard–M.I.T. Division of Health Sciences and Technology (Feb. 1990).

Nyilas, E., et al, "Peripheral Nerve Repair with Bioresorbable Prosthese," *Trans. Am. Soc. Artif. Intern. Organs*, 29:307–313 (1983).

O'C. Hamilton, Joan, "Miracle Cures May be in Your Cells," *BusinessWeek* (Dec. 6, 1993).

O'Donnell & Puri, "Treatment of Vesicoureteric Reflux by Endoscopic Injection of Teflon," *British Medical Journal* 289:7–9 (Jul. 7, 1984).

Oliwenstein, L., "The Power of Plastics," *Discover* p. 18 (Dec., 1989).

Patterson & Gage, "Adrenal Chromaffin Cell–Derived Cholinergic Neurons for Brain Transplants," *Caltech Biology* pp 201–202 (1987).

Puelacher, W. C., et al., "Tissue–Engineered Growth of Cartilage: the Effect of Varying the Concentration of Chondrocytes Seeded onto Synthetic Polymer Matrices," *Int. J. Oral Maxillofac. Surg.*, 23:49–53 (1994).

Rames & Aaronson, "Migration of Polytef Paste to the Lung and Brain Following Intravesical Injection for the Correction of Reflux," *Pediatric Surgery* 6(1):239–240 (Jan., 1991).

Redmond, D. E. Jr., et al., "Transplants of Primate Neurons," *The Lancet*,2(8510):1046 (Nov. 1, 1986).

Reid, L. M., et al. "Long–Term Cultures of Normal Rat Hepatocytes on Liver Biomatrix," *Ann. NY Acad. Sci.* 349:70–76 (1980).

Retik, A. B., et al., "Management of Severe Hypospadias with a 2–Stage Repair," *Microbiology & Immunology* 152:749–751 (Aug., 1984).

Rhine, W. D., et al., "Polymers for Sustained Macromolecule Release: Procedures to Fabricate Reproducible Delivery Systems and Control Release Kinetics," *Journal of Pharmaceutical Sciences*, 69(3):265–269 (Mar., 1980).

Rosen, H. B., "Bioerodible Polyanhydrides for Controlled Drug Delivery," 1983 Butterworth & Co. (Publishers) Ltd.

Sapozhnikova, M. A., et al., "Morphological Changes in Splenic Autografts Following Splenectomy: Experimental and Clinical Findings," *Biological Abstracts*, 86(76896) (1987).

Sasaki, K., "Neovascularization in the Splenic Autograft Transplanted into Rat Omentum as Studied by Scanning Electron Microscopy of Vascular Casts," *Virchows Arch.*, 409:325–334 (1986).

Sawada, N., et al., "Effects of Extracellular Matrix Components on the Growth and Differentiation of Cultured Rat Hepatocytes," *In Vitro Cellular & Development Biology*, 23(4): 267–273 (Apr., 1987).

Seckle, "Nerve Regeneration Through Synthetic Biodegradable Nerve Guides: Regulation by the Target Organ," *Plast. Reconstr. Surg.*, 74(2):173–81 (Aug., 1974).

Siegel & Langer, "Controlled Release of Polypeptides and Other Macromolecules," *Pharmaceutical Research*, pp 2–10 (1984).

Sladek, J. R., Jr., et al., "Survival and Growth of Fetal Catecholamine Neurons Transplanted Into Primate Brain," *Brain Research Bulletin*, 17:809–818 (1986).

Sladek & Shoulson, "Neural Transplantation: A Call for Patience Rather Than Patients," *Science*, 240:386–388 (Jun. 10, 1988).

Sladek, J. R., "Transplantation of Fetal Dopamine Neurons in Primate Brain Reverses MPTP Induced Parkinsonism," *Progress in Brain Research*,71:309–323 (1987).

Stemple, Derek L. *Altech Biology* (1987).

Tachibana, Masaaki, "Ureteral Replacement Using Collagen Sponge Tube Grafts," *The Journal of Urology* 133(4):866–869 (Apr., 1985).

Tavassoli, M., et al., "Studies on Regeneration of Heterotopic Splenic Autotransplants," *Blood*, 41(5):701–709 (May, 1973).

Thompson, J. A., "Implantable Bioreactors: Modern Concepts of Gene Therapy," *Current Communications in Molecular Biology*, Daniel Marshak, et al., editors, pp 143–147 (Cold Spring Harbor Laboratory, 1989).

Thuroff, J., et al., "Cultured Rabbit Vesical Smooth Muscle Cells for Lining of Dissolvable Synthetic Prosthesis," *Urology*, 21(2):155–158 (1983).

Unipoint Industries, Inc., "Polyvinyl Alcohol Foam for Surgical And Industrial Use," Product Review.

UNOS Update, "National Cooperative Transplantation Study Completed," 7(10) (Oct./Nov. 1991).

Vacanti, J. P. et al., "Engineered Bone from Polyglycolic Acid Polymer Scaffold and Periosteum," (abstract) Materials Research Society, (Apr. 17–21, 1985).

Vacanti, C. A., et al., "Formation of New Cartilage in Vivo by Implantation of Cell–Polymer Constructs Created in Vitro,".

Vargo, Rita L., "Infection as a Complication of Liver Transplant," *Critical Care Nurse* 9(4):52–62.

Vijg, J., et al., "UV–Induced DNA Excision Repair in Rat Fibroblasts During Immortalization and Terminal Differentiation in Vitro," *Exp. Cell. Res.* 167:517–530 (1986).

Vorstman, Bert, et al., "Polytetrafluoroethylene Injection for Urinary Incontinence in Children," *The Journal of Urology* 133(2):248–250 (Feb., 1985).

Walker, R. D., et al., "Injectable Bioglass as a Potential Substitute for Injectable Polytetrafluoroethylene," *The Journal of Urology* 148(1):645–647.

Walton & Brown, "Tissue Engineering of Biomaterials for Composite Reconstruction: An Experimental Model," *Annals of Plastic Surgery* 30(2):104–110 (Feb., 1993).

Yannas & Burke, "Design of an Artificial Skin. I. Basic Design Principles," *Journal of Biomedical Materials Research* 14:65–81 (1980).

Yannas, I. V., et al., "Regeneration of Sciatic Nerve Across 15 mm Gap by Use of a Polymeric Template," *Polym. Sci. Technol. Iss. Adv. Biomed. Polymer* 35:109 (1987).

Yannas and Orgill, "Polymeric Template Facilitates Regeneration of Sciatic Nerve Across 15 MM Gap," *Polymer. Material Sci. Eng.* 53:216–218 (1985).

Yannas, I. V., et al., "Suppression of in Vivo Degradability and of Immunogenicity of Collagen by Reaction with Glycosaminoglycans," *Polymer. Prepar. Am. Chem. Soc. Div. Polym. Chem.*, 16(2): 209–214 (1975).

Yannas, I. V., "Wound Tissue Can Utilize a Polymeric Template to Synthesize a Functional Extension of Skin," *Science* 215:174–176 (1982).

Report of the International Reflux Study Committee, "Medical Versus Surgical Treatment of Primary Vesicoureteral Reflux: A Prospective International Reflux Study in Children," *The Journal of Urology* 125:277–283 (Mar., 1981).

Zund, G., et al., "A New Approach for a Bioprothetic–Heart Valve," The European Association for Cardio–Thoracic Surgery, (Jan. 31, 1995).

Anderson, David J., *Caltech Biology*, 1987.

Atala & Casale, "Management of Primary Vesicoureteral Reflux," *Infections in Urology* pp 39–43 (Mar./Apr., 1990).

Henley, D. R., et al., "Particulate Silicone for Use in Periurethral Injections: A Study of Local Tissue Effects and a Search for Migration," *The J. of Urol.*, 147(4):376a Abstract No. 654 (Apr., 1992).

Iacovou, J., et al., "Periurethral Silicone Microimplants for the Treatment of Simple Stress Incontinence," *The J. of Urol.,* 147(4):376a Abstract No. 655 (Apr., 1992).

Patsias, G., et al., "Transurethral Polytef Injection in Females with Urinary Incontinence," *The J. of Urol.,* 147(4):376a Abstract No. 656 (Apr., 1992).

Bazeed, Mahmoud, et al. "New Surgical Procedure for Management of Peyronie Disease," *Urology* 21(5), 501–504 (1983).

Berrino, Pietro, et al. "Surgical Correction of Breast Deformities Following Long–Lasting Complications of Polyurethane–Covered Implants," *Ann. Plast. Surg.,* 24:481 (1990).

Bissell, D. Montgomery, et al., "Interactions of Rat Hepatocytes with Type IV Collagen, Fibronectin and Laminin Matrices, Distinct Matrix–Controlled Modes of Attachment and Spreading," *European Journ. of Cell Biology* 40:72–78 (1986).

Bissell, D. M., et al. "The Role of Extracellular Matrix in Normal Liver," *Scand. J. Gastroenterol.,* 23:107 (1988).

Bissell, D. Montgomery, "Support of Cultured Hepatocytes by Laminin–Rich Gel," *J. Clin. Invest.* 79:801–812 (1987).

Bjorklund, *Annals of the N.Y. Academy of Science* 495:676–686 (1987).

Bohn, Martha C., et al., "Adrenal Medulla Grafts Enhance Recovery of Striatal Dopaminergic Fibers," *Science* 238(4817):913–916 (Aug. 21, 1987).

Burke, "The Effects of the Configuration of an Artificial Extracellular Matrix on the Development of a Functional Dermis," *The Role of Extracellular Matrix in Development* 351–355 (Alan R. Liss, Inc., NY 1984).

Collier, T. J., et al., "Norepinephrine Deficiency and Behavioral Senescence in Aged Rats: Transplanted Locus Ceruleus Neurons as an Experimental Replacement Therapy," *Annals of the New York Academy of Science* 495:393–403 (1987).

Davis, George E., et al., "Human Amnion Membrane Serves as a Substratum for Growing Axons in Vitro and in Vivo," *Science,* 236:1106–1109 (May 29, 1987).

Gash, D. M., et al., "Amitotic Neuroblastoma Cells Used for Neural Implants in Monkeys," *Science* 233(4771):1420–2 (Sep. 26, 1986).

Gash, D. M., "Neural Transplantation: Potential Therapy for Alzheimer's Disease," *J. Neural Trans. [Suppl]* 24:301–8 (1987).

Grande, Daniel A., et al., "The Repair of Experimentally Produced Defects in Rabbit Articular Cartilage by Autologous Chondrocyte Transplantation," (May 11, 1988).

Groth, C. G., et al., "Correction of Hyperbilirubinemia in the Glucoronyltransferase–Deficient Rat by Intraportal Hepatocyte Transplantation," *Transplant. Proc.* 9:313–316 (1977).

Henry, E. W., et al., "Nerve Regeneration Through Biodegradable Polyester Tubes," *Exp. Neurol.* 90(3): 652–676 (Dec., 1985).

Ingber, D. E., et al., "Cells as Tensecrity Structures: Architectural Regulation of Histodifferentiation by Physical Forces Transduced Over Basement Membrane," *Gene Expression During Normal and Malignant Differentiation,* L. C. Anderson, et al., editors, pp 13–32 (Academic Press, Orlando, FL 1985).

Ingber, et al., "Control of Capillary Morphogenesis: A Molecular System of Mechanical Switches," *J. Cell Biol.,* 107:797a (1988).

Jacksic, et al., "The Use of 'Artificial Skin' for Burns," *Ann. Rev. Med.* 38:107–116 (1987).

Jaurequi, H. Q. et al., "Attachment and Long Term Survival of Adult Rat Hepatocytes in Primary Monolayer Cultures: Comparison of Different Substrata and Tissue Culture Medial Formulations," *In Vitro Cellular & Development Biology,* 22(1):13–22 (Jan. 1986).

Kleinman, H. K., et al., "Use of Extracellular Matrix Components and Cell Culture," *Analytical Biochemistry* 166:1–13 (1987).

Kordower, J. H., et al., "Neuroblastoma Cells in Neural Transplants: A Neuroanatomical and Behavioral Analysis," *Brain Research,* 417:85–98 (1987).

Lewin, "Cloud Over Parkinson's Therapy," *Science News,* 240: 390–392 (1988).

Li, M. L., et al., Influence of a Reconstituted Basement Membrane and its Components of Casein Gene Expression and Secretion in Mouse Mammary Epithelial Cells,: *Proc. Natl. Acad. Sci. USA,* 84:136–140 (1987).

Madison, R. et al., "Increased Rate of Peripheral Nerve Regeneration Using Bioresorbable Nerve Guides and Lamin–Containing Gel," *Exp. Neurol.,* 88(3) 767–772 (Jun. 1985).

Madison, R., et al., "Peripheral Nerve Regeneration with Entubulation Repair: Comparison of Biodegradeable Nerve Guides Versus Polyethylene Tubes and the Effects of a Laminin–Containing Gel," *Exp. Neurol.* 95(2)387–390 (Feb., 1987).

Michalopoulos & Pitot, "Primary Culture of Parenchymal Liver Cells on Collagen Membranes," *Exper. Cell. Res.* 94:70–78 (1975).

Minato, et al., "Transplantation of Hepatocytes for Treatment of Surgically Induced Acute Hepatic Failure in the Rat," *Eur. Surg. Res.,* 16:162–169 (1984).

Mounzer, A. M., et al., "Polyglycolic Acid Mesh in Repair of Renal Injury," *Urology* 28(2):172–130 (1986).

Movitz, David, "Accessory Spleens and Experimental Splenosis Principles of Growth," *The Chicago Medical School Quarterly,* 26(4):183–187 (Winter–Spring 1967).

Naughton, B. et al., Granulopoiesis and Colony Stimulating Factor Production in Regenerating Liver, *Exp. Hematol.,* 10(5):451–458 (May, 1982).

Notter, M. F., et al, "Neuronal Properties of Monkey Adrenal Medulla in vitro," *Cell Tissue Res.,* 244(1):69–76 (1986).

Oellrich, R. G., et al. "Biliary Atresia," Neonatal Network pp 25–30 (Apr., 1987).

Omery, Anna, "A Nursing Perspective of the Ethical Issues Surrounding Liver Transplantation," *Heart & Lung* 17(6):626–630 (Nov., 1988).

Pasik, P., *Annals of the N.Y. Academy of Science,* 495:674–675 (1987).

Pimpl, et al., "Experimentelle Studie zur Frage der Transplantatkonditionierung und Transplantatgrofe bei heterotoper autologer Milztransplantation," *Lagenbecks Archiv* 37215–36218 (Salzburg 1984).

Ptasinska–Urbanska, et al, "Intrascleral Introduction of Isolated Allogeneic Chondrocytes Capable of Cartilage Reformation in Rabbits; Possible Procedure in Treatment of Detachment of the Retina," *Exp. Eve. Res.,* 24(3):241–247 (1977).

Rosen, H. B., "Bioerodible Polymers for Controlled Release Systems," *Controlled Release Systems: Fabrication Technology,* 11:83–110.

Schmeck, H. M., Jr., "Doctors try to Capitalize on the Liver's Ability to Regenerate Itself," *The New York Times Medical Science,* (May 16, 1989).

Selden, C., et al., "The Pulmonary Vascular Bed as a Site for Implantation of Isolated Liver Cells in Inbred Rats," *Transplantation*, 38(1):81–83 (Jul., 1984).

Shine, H. D., et al., "Cultured Peripheral Nervous System Cells Support Peripheral Nerve Regeneration Through Tubes in the Absence of Distal Nerve Stump," *Journal of Neuroscience Research*, 14:393–401 (1985).

Sutherland, D. E., et al., "Hepatocellular Transplantation in Acute Liver Failure," *Surgery* 82(1):124–132 (Jul. 1977).

Sommer, B. G., et al., "Hepatocellular Transplantation for Treatment of D–Galactosamine–Induced Acute Liver Failure in Rats," *Transplant. Proc.*, 11(1):578–584 (Mar., 1979).

Strom, S. C., et al., "Isolation, Culture, and Transplantation of Human Hepatocytes," *JNCL*, 68(5):771–778 (May 1982).

Sudhakaran, P. R., et al., "Modulation of Protein Synthesis and Secretion by Substratum in Primary Cultures of Rat Hepatocytes," *Exper. Cell Res.* 167:505–516 (1986).

Sullivan, Walter, "Spinal Injury Research Yields a Glimmer of Hope," *The New York Times* p.C6 (Jul. 14, 1987).

Thompson, J. A., "Heparin–Binding Growth Factor 1 Induces the Formation of Organoid Neovascular Structures in Vivo," *Proc. Natl. Acad. Sci USA*, 86:7928–27932 (Oct., 1989).

Tomomura, A., et al, "The Control of DNA Synthesis in Primary Cultures of Hepatocytes From Adult and Young Rats: Interactions of Extracellular Matrix Components, Epidermal Growth Factor, and the Cell Cycle," ©1987 Alan R. Liss, Inc.

Upton, J., et al., Neocartilage Derived from Transplanted Perichondrium: What is it? *Plastic and Reconstructive Surgery* 68(2): 166–174 (1981).

Vacanti, J. P., "Beyond Transplantation," *Arch. Surgery* 123:545–549 (May 1988).

Vroemen, J. P., et al., "Hepatocyte Transplantation for Enzyme Deficiency Disease in Congenic Rats," *Transplantation* 42(2):130–135 (1986).

Wozney, J. M., et al., "Novel Regulators of Bone Formation: Molecular Clones and Activities," *Science*, 242:1528–1534 (Dec., 16, 1988).

Yannas and Orgill, "Artifical Skin: A Fifth Route to Organ Repair and Replacement," *Iss. Polym. Biomaterial*, 106:221–230 (1986).

Alberts, Bruce, et al *Molecular Biology of The Cell* Garland Publishing, Inc., pp.893–894.

Allcock, H. R., et al., "Synthesis of Poly[(Amino Acid Alkyl Ester)Phosphazenes]$^{1-3}$" –*Macromolecules* 10(4) (Jul./Aug. 1977).

Allcock, H.R., et al., "Hydrolysis Pathways for Aminophosphazenes$^1$," *Inorg.Chem.* 21(1):515–521 (Jan. 1982).

Allcock, H. R., et al., "Amphilphilic Polyphosphazenes as Membrane Materials: Influence of Side Group on Radiation Cross Linking," *Biomaterials* 9(6):500–508 (Nov. 1988).

Allcock & Kwon, "An Ionically Cross–Linkable Polyphosphazene: Poly[bis(carboxylatophenoxy)phosphazene] and Its Hydrogels and Membranes," *Macromolecules* 22:75–79 (1989).

Blaives Jerry, et al., "When Sphincter Failure is the Cause of Female Stress Incontinence," *Comtemporary Urology* 5(3):33–54 (Mar., 1993).

Elkowitz, A., et al., "Various Methods of Breast Reconstruction After Mastectomy: An Economic Comparison," *Plastic and Reconstructive Surgery*, 92(1):77–83 (Jul. 1993).

Erickson, Deborah, "Material Help," *Scientific American* pp 114–116 (Aug. 1992).

Geiss, S., et al "Multicenter Survey of Endoscopic Treatment of Vesidoureteral Reflux in Children," *Eur. Urol* 17:328–329 (1990).

Grande, Daniel A., et al., "Healing of Experimentally Produced Lesions in Articular Cartilage Following Chondrocyte Transplantation," *The Anatomical Record* 218:142–148 (1987).

Green, Howard, "Growth of Cultured Human Epidermal Cells into Multiple Epithelia Suitable for Grafting," *Proc. Natl. Acad. Sci. USA* 76(11):5665–5668 (Nov., 1979).

Lucas, P., et al, "Ectopic Induction of Cartilage and Bone by Water–Soluble Proteins from Bovine Bone Using a Poclyanhydride Delivery Vehicle," *Journal of Biomedical Materials Research* 24(7):901–911 (1990).

Matas, et al., "Hepatocellular Transplantation for Metabolic Deficiencies: Decrease of Plasma Bilirubin in Gunn Rats," *Science* 192:892–894 (1978).

Naughton, B., et al., "Long–Term Growth of Rat Bone Marrow Cells in a Three–Dimensional Matrix" Medical Laboratory Sciences Department, Hunter College School of Health Sciences, New York, *The Anatomical Record*, 218(1):97a (May, 1987).

Naughton, G., et al., "Erythropoietin Production by Macrophages in the Regenerating Liver," *Journal of Surgical Oncology* 30:184–197 (1985).

O'Connor, N., et al., "Grafting of Burns with Cultured Epithelium Prepared from Autologous Epidermal Cells," *The Lancet*, 1(8210):75–78 (Jan., 1981).

Perlow, M. J., "Brain Grafting as a Treatment for Parkinson's Disease," *Neurosurgery* 20(2):335–342 (1987).

Pimpl, et al., "Perfusion of Autologous Splenic Grafts in Correlation with Specific Immunological Functions An Experimental Study in Pigs," *Eur. Surg. Res.* 19:53–61 (1987).

Pitman, M. I., et al., "The Use of Adhesives in Chondrocytes Transplantation Surgery: In–Vivo Studies," *Bulletin of the Hospital for Joint Diseases Orthopaedic Institute* 49(2):213–220 (1989).

Van der Kwaar, T. H., et al., "Establishment and Characterization of Long–Term Primary Mouse Urothelial Cell Cultures," *Urological Research*, 17(1):290–293 (1989).

Whitaker, Robert., "Scientists Growing Tissue From 'Seed'," *The Boston Globe* (Monday, Feb. 22, 1993).

Yannas, I. V., "What Criteria Should be Used for Designing Artificial Skin Replacement and How Well do the Current Grafting Materials Meet These Criteria?" *J. of Trauma*, 24(9):929–939 (1984).

Matouschek P., "Die Behandlung des vesilorenalan Refluxes durch transueterale Einspritzung von polytetrafluorothylenepast", *Urologe*, 20:263 (1981).

Matsuda et al., "Photoinduced Prevention Of Tissue Adhesion", *ASAID Trans.*, 38:154–157 (1992).

Steinleitner, et al., "Poloxamer 407 As An Intraperitoneal Barrier Material For The Prevention of Postsurgical Adhesion Formation And Reformation In Rodent Models For Reproductive Surgery", *Obstetrics and Gynecology*, 77:48–52 (1991).

Steinleitner, et al., "An Evaluation Of Flowgel As An Intraperitoneal Barrier For Prevention Of Postsurgical Adhesion Reformation", *Fertility and Sterility*, 57:305–308 (1992).

Culliton, Barbara J., "Gore Tex Organoids and Genetic Drugs," *Science* 246:747–749 (1989).

Ingber, D. E., "How Does Extracellular Matrix Control Capillary Morphogenesis?" *Cell* 58:803–805 (Sep. 8, 1989).

Ingber, D. E., et al., "Mechanochemical Switching Between Growth Factor–Stimulated Angiogenesis In Vitro: Role of Extracellular Matrix," *J. Cell. Biol.,* 109:317–330 (1989).

Kordower, J. H. et al., "An In Vivo and In Vitro Assessment of Differentiated Neuroblastoma Cells as a Source of Donor Tissue for Transplantation," *Annals of The New York Academy of Sciences,* 495:606–622 (new York 1987).

Kretschmer, et al., "Autotransplantation of Pancreatic Fragments to the Portal Vein and Spleen of Total Pancreatectomized Dogs," *Ann. Surg.,* 187:79–86 (Jan., 1978).

Kusano, et al., *Acta Japoni Hepato* 63:345–351 (1989).

Letourneau, Paul C., "Possible Roles of Cell–to–Substratus Adhesion in Neuronal Morphogenesis," *Developmental Biology,* 44:77–91 (1975).

Madison, R., et al., "Nontoxic Nerve Guide Tubes Support Neovascular Growth in Transected Rat Optic Nerve," *Exp. Neurol.* 86:448–461 (1984).

Mesnil, M., et al., "Cell Contact but Not Junctional Communication (Dye Coupling) with Biliary Epithelial Cells is Required for Hepatocytes to Maintain Differentiated Functions," *Exper. Cell Res.* 173:524–533 (1987).

Naji, et al., "Successful Islet Transplantation in Spontaneous Diabetes," *Surgery* 86:218–226 (1979).

Redmond, D. E., Jr., et al., "Fetal Neuronal Grafts in Monkeys Given Methyphenyltetrahydropyridine," *The Lancet,* pp 1125–1127 (May 17, 1986).

Schubert & Baird, "Multiple Influences of a Heparin–Binding Growth Factor for Neuronal Development," *The Journal of Cell Biology,* 104:635–643 (Mar. 1987).

Sirica, A., et al., "Fetal Phenotypic Expression by Adult Rat Hepatocytes on Collagen Gel/Nylon Meshes," *Proc. Natl. Acad. Sci. USA,* 76(1):283–287 (Jan., 1979).

Sirica, A., et al., "Use of Primary Cultures of Adult Rat Hepatocytes on Collagen Gel–Nylon Mesh to Evaluate Carcinogen–Induced Unscheduled DNA Synthesis," *Cancer Research,* 40:3259–3267 (Sep. 1980).

Sladek, J. R., Jr., et al, "Reversal of Parkinsonism by Fetal Nerve Cell Transplants in Primate Brain," *Annals of the New York Academy of Sciences,* 496:641–657 (1987).

Mito, et al., "Hepatocellular Transplantation," Department of Surgery, Asahikawa Medical College 078 4–5 Nishi–Kagura, Asahikawa, Japan.

Berrino, Pierro, et al. "Surgical Correction of Breast Deformities Following Long–Lasting Complications of Polyurethane–Covered Implants," *Ann. Plast. Surg.,* 24:481 (1990).

Bjorklund Annais of the N.Y. Academy of Science 495:676–686 (1987).

Bohn Martha C. et al., "Adrenal Medulla Grafts Enhance Recovery of Striatal Dopaminergic Fibers" Science 238(4817):913–916 (Aug. 21, 1987).

Gash D.M. et al., "Amitotic Neuroblastoma Cells Used for Neural Implants in Monkeys" Science 235(4771):1420–1422.

Gash D.M. et al., "Neural Transplantation: Potential Therapy for Alzheimer's Disease"J. Neural Trans. (Suppl) 24:301–308 (1987).

Gains S. et al., "Multicenter Survey of Endoscopic Treatment of Vesidouretaral Reflux in Children" Fur Urgl. 17:328–329.

Grande Daniel A et al., "The Repair of Expermentally Produced Defectes in Rabbit Articular Cartilage by Autologous Chondrocyte Transplanatation," (May 11, 1988).

Madison R. et al., "Increased Rats of Peripheral Nerve Regeneration Using Biorssorable Nerve Guides and Lamin- -Containing Gel," *Exp. Neurol.,* 88(3) 767–772 (Jun. 1985).

Madison R et al., "Panaberal Nerve Regeneration with Entublation Repair: Comparison of Biodegradeable Nerve Guides Versus Polyethylene Tubes and the Effects of a Laminin–Containing Gel," *Exp. Neurol* 95(2)387–390 (Feb. 1987).

Michalopoulgs & Pitat "Primary Culture of Paranchynal Liver Cells on Collagen Membranes," Exper. Cell. Res. 94:70–75 (1975).

Minato et al., "Transplanatation of Hepatocytes for Treatment of Surgically Induces Acute Hepatic Failure in the Rat," *Eur. Surg. Res.* 16:162–169 (1984).

Naughton B. et al., Granulopoiesis and Colcony Stimulating Factor Production in Regenerating Liver, Exp. Hematol., 10(5):451–458 (May, 1982).

Notter, M.F., et al, "Neuronal Properties of Monkey Adrenal Medulla in vitro," *Cell Tissue Res.,* 244(1):69–76 (1986).

Pasik, P. *Annals of the N.Y. Academy of Science* 495:674–675 (1987).

Parlow M.J. "Brain Graftine as a Treatment for Parkinson's Disease," Neurosurgery 20(2):335–342 (1987).

Pimpl et al., "Perfusion of Autologous Splenic Grafts on Correlation with Specific Immunological Functions An Expermental Study in Pigs," *Eur. Surg. Res.* 19:53–61 (1987).

Ptasinska–Urbanaka et al., "Intraselerol Introduction of Isolated Allogeneic Chondrocytes Capable of Cartilage Reformation in Rabbits; Possible Procedure in Treatment of Detachment of the Retina," *Int. J. Oral Maxillofac. Surg.,* 23:49–53 (1994).

Sladek, J. R., Jr., et al., "Survival and Growth of Fetal Cateecholamine Neurons Traspalnted Into Primate Brain," *Brain Research Bullentin,* 17:809–818 (1986).

Sladek, J. R., Jr., et al. "Reversal of Parkinsonism by Fetal Nerve Cell Transplants in Primate Brain," *Annals of the New York Academy of Sciences,* 495:641–657 (1987).

Stemple, Derek L. Altech Biology (1987).

Sudkahakaran P. R. et al., "Modulation of Protein Synthesis and Secretion by Substratum in Primary Cultures of Rat Hepatocytes,"*Exper. Cell. Res.* , 167:505–516 (1986).

Sullivan, Walter, "Spinal Injury Research Yields a Gilmmer of Hope,"T *The New York Times*p. C6 (Jul. 14, 1987).

Thomspon J. A., "Implantable Bioreactors: Modern Concepts of Gene Therapy," Current Communications in Molecular *Biology,* Daniels Marshak, et al., editors, pp. 143–147 (Cold Spring Harbor Laboratory, 1989).

Tomomura, A., et al., "The Control of DNA Synthesis in Primary Cultures of Hepatcytes From Adult and Young Rats: Interactions of Extracelluar Matrix Components, Epidermal Growth Factor, and the Call Cycle," ©1987 Alan R. Liss, Inc.

Upton J. et al., Neucartilage Derived from Transplanted Perichondrium: What is it?Plastic and Reconstructive Surgery 68(2): 166–174 (1981).

Vacanti J. P. "Beyond Transplanatation" *Arch Surgery*123:545–549 (May 1988).

Vrocman, J. P. et al., "Hepatocyte Transplantation for Enzyme Deficiency Diseases in Congenic Rats, " *Transplantation,* 42(2):130–135 (1986).

Wozney, J. M. et al., "Novel Regulates of Bone Formation: Molecular Clones and Activates," Science, 242:1528–1534 (Dec. 16, 1988).

Yannas and Orgill, "Polymeric Template Faciltates Regeneration of Sciatic Nerve Across 15 MM Gap,"Polymer.*Materials Sci. Eng.* 53:216–218 (1985).

Alberta, Bruce, et al., *Molecular Biology of the Cell* Garland Publishing, Inc. pp. 893–894.

Burke, "The Effects of the Configuration of an Articifical Extracellar Matrix on the Developmenty of a Functional Dermis," *The role of Extracellular Matrix in Development* 351–355 (Alan R. Liss, Inc., NY 1984).

Collier, T. J. et al., "Norepinephrine Deficiency and Behavioral Senescence in Aqed Rats: Transplanted Locus Ceruleus Neurons as an Expermental Replacement Therapy," *Annals of the New York Academy of Science* 495:396–403 (1987).

Groth, C. G. et al., "Correction of Hyperbilirubinemia in the Glucoronytransferase–Deficient Rat by Intraportal Hepatocyte Transplantation," *Transplant. Proc.* 9:313–316 (1977).

Henry, E. W. et al., "Nerve Regeneration Through Biodegradable Polyster Tubes," *Exp. Neurol.* 90(3):652–676 (Dec. 1985).

Ingber, et al., "Control of Capillary Morphogensis: A Molecular System of Mechanical Switches," *J. Cell. Biol.*, 107–797a (1988).

Jacksic, et al., "The Use of Articifical Skin for Burns," Ann. Rev. Med. 38:107–116 (1987).

Jeurequi, H. O., et al., "Attachment and Long Terms Survival of Adult Rat Hepatocytes in Primary Monolayer Cultures: Comparison of Different Substrates and Tissue Culture Medical Formulations," *In Vitro Cellular & Development Biology*, 22(1):13–22 (Jan. 1986).

Kleinman, II. K. et al., "Use of Extracellular Matrix Components and Cell Culture," *Analytical Biochemistry* 166:1–13 (1987).

Kordower J. H., et al., "Neurblastoma Cells in Neurol Transplants: A Neuroanatomiocal and Behavior Analysis," *Brain Research*, 417:85–98 (1987).

Lewin, "Cloud Over Parkinson's Therapy," Science News, 240, 390–392 (1988).

Li. M. I. et al., Influence of a Reconstituted Basement Membrane and its Components of Casein Gene Expression and Secretion in Mouse Mammary Epithelial Cells,; *Proc. Natl. Acad. Sci. USA* 84:136–140 (1987).

Madison R. et al., "Increased Rate of Peripheral Nerve Regeneration Using Biosorable Nerve Guides and Lamin--Containing Gel," *Exp. Neurol.*, 88(3) 767–772 (Jun 1985).

Madison R. et al., "Perpheral Nerve Regeneration With Entubulation Repair: Comparison of Biodegradeable Nerve Guides Versus Polyethylene Tubes and the Effects of a Laminin–Containing Gel," *Exp. Neurol.* 95(2)387–390 (Feb. 1987).

Michalopoulos & Pitot, "Primary Culture of Paronchymal Liver Cells on Collagen Membranes," *Exper. Cell. Res.* 94:70–78 (1975).

Minato, et al., "Transplanatation of Hepatocytes for Treatment of Surigically Induced acuta Hepatic Failure in the Rat," *Eur. Surg Res.*, 16:162–169 (1984).

Mounzer A. M. et al., "Polyglycolic Acid Mean in Repair of Renal Injury" Urology 28(2):177–130 (1985).

Osilrich, R. G. et al., "Bilary Atrasis" Neonetal Networks pp. 25–30 (Apr. 1987).

Omery, Anna. "A Nursing Perspective of the Ethical Issues Surrounding Liver Transplantation," Heart & Lung 17(5):625–630 (Nov. 1988).

Pasik P. Annals of the N. Y. Academy of Science 495:674–675 (1987).

Rosen M. B. "Bioerodible Polymers for Controlled Release Systems," Controlled Release Systems: Fabrication Technology 11;93–110.

Schmack H. M. Jr. "Doctors try to Capitalize on the Liver'Ability to Regerenate Itself" *The New York Times Medical Science* (May 16, 1989).

Saiden, C. et al., "The Pulmonary Vascular Bed as a Site for Implantation of Isolated Liver Cells inbred Rats," Transplanatation 38(1)81–83 (Jul, 1984).

Shine, H. D. et al., "Cultured Peripheral Nervous System Cells Support Peripheral Nerve Regeneration Through Tubes in the Absence of Digital Nerve Stump," *Journal Of Neuroscience Research*, 14:393–401 (1985).

Sommer, B. G. et al., "Hepatocellular Transplantation for Treatment of D–Galactosamine–Induced Acute Layer Failure in Rats", *Transplant. Proc.*, 11(1):578–584 ( Mar. 1979).

Strom, S. C. et al., "Isolation Culture and Transplantation of Human Hepatocytes," JNCL. 88(5);771–778 (May 1982).

Sudhakaran, P. R. et al., "Modulation of Proteins Synthesis and Secretion by Substratum in Primary Cultures of Bar Hepatocytes," *Exper. Cell. Res.* 167:505–516 (1986).

Sullivan, Walter "Spinel Injury Research Yields a Gimmer of Hope," The New York Times p. C6 (Jul. 14, 1987).

Thompson, J. A. "Hepario–Binding Growth Factor 1 induces the Formation of Organoid Neovascular Structures in Vivo," *Proc. Natl. Acad. Sci. USA*, 86:7928–27932 (Oct. 1989).

Tormomurs, A. et al., "The Controls of DNA Synthesis in Primary Cultures of Hepatocytes From Adult and Young Rats: Interactions of Extracellular Matrix Components, Epidermal Growth Factor, and the Cell Cycle" å1987 Alan R. Liss, Inc.

INJECTABLE HYDROGEL COMPOSITIONS

BACKGROUND OF THE INVENTION

The present invention is generally in the area of using polymeric hydrogel-cell compositions in medical treatments.

Craniofacial contour deformities

Craniofacial contour deformities, whether traumatic, congenital, or aesthetic, currently require invasive surgical techniques for correction. Furthermore, deformities requiring augmentation often necessitate the use of alloplastic prostheses which suffer from problems of infection and extrusion. A minimally invasive method of delivering additional autogenous cartilage or bone to the craniofacial skeleton would minimize surgical trauma and eliminate the need for alloplastic prostheses. If one could transplant via injection and cause to engraft large numbers of isolated cells, one could augment the craniofacial osteo-cartilaginous skeleton with autogenous tissue, but without extensive surgery.

Unfortunately, attempts to inject dissociated cells subcutaneously or to implant dissociated tissues within areas of the body such as the peritoneum have not been successful. Cells are relatively quickly removed, presumably by phagocytosis and cell death.

Cells can be implanted onto a polymeric matrix and implanted to form a cartilaginous structure, as described in U.S. Pat. No. 5,041,138 to Vacanti, et al., but this requires surgical implantation of the matrix and shaping of the matrix prior to implantation to form a desired anatomical structure.

Vesicoureteral reflux.

Vesicoureteral reflux is a condition wherein there is an abnormal development of the ureteral bud as it enters the bladder during embryologic development. The shortened course of the ureter through the bladder musculature decreases the ureteral resistance and allows for urine to reflux from the bladder reservoir back up into the ureter and into the kidney. With this condition, bacteria which may occasionally be present in the bladder through retrograde urethral transport, can reach the kidneys and cause recurrent pyelonephritis. In addition, the constant back pressure of the urine into the calyces and renal pyramids results in mechanical damage to the renal parenchyma. If untreated, urinary vesicoureteral reflux can cause loss of renal parenchyma, and in some instances, renal failure, as reviewed by Atala and Casale, *Infections in Urology* 39–43 (March/April 1990). In 1960, 70% of the patients with renal failure were described as having vesicoureteral reflux as the primary etiology. With the advent of new diagnostic and treatment modalities, patients with vesicoureteral reflux now account for less than 1% of the renal failure population.

In the past, vesicoureteral reflux was usually diagnosed with a voiding cystogram after the child presented with repeated episodes of pyelonephritis. With the increased use of prenatal and postnatal sonography, hydronephrosis is more detectable, prompting further radiologic workup and earlier detection, as reported by Atala and Casale. Vesicoureteral reflux is graded depending on the severity. Grade 1 reflux signifies that urine is seen refluxing from the bladder up to the ureter only; in grade 2 reflux, urine refluxes into the ureter and calyceal dilatation. Grade 4 and 5 reflux are more severe, showing ureteral tortuosity and further calyceal blunting and dilatation, respectively.

The treatment of vesiciourateral reflux has been well established over the last decade. Initially it was believed that all patients with reflux would require surgery. Another school of management soon proposed that only medical therapy with antibiotics was required. It is now well established that the treatment of reflux depends on many factors, including the severity of reflux, associated congenital abnormalities, and the social situation of the child (parental compliance with medical treatment). Medical treatment is usually recommended for patients with grade 1 and 2 reflux, which usually resolve on their own as the bladder/ureteral configuration changes with growth. Grade 3 reflux is generally managed with medical therapy unless it persists or breakthrough infections occur while on antibiotic suppression. Surgical treatment is usually required for grade 4 and 5 reflux.

Medical treatment implies that the patient is treated with daily suppressive antibiotics. A close follow-up is required in these patients, generally consisting of a catheterized urine culture every three months, an ultrasound exam and serum analysis every six months, a fluoroscopic or nuclear voiding cystourethrogram every year, and a DMSA renal scan every two years. Surgical treatment consists of an open surgery wherein a low abdominal incision is made, the bladder is entered, the ureters are mobilized and new ureteral submucosal tunnels are created; thereby extending the muscular backing of the ureter which increases their resistance. These patients require a general endotracheal anesthetic for a four to five hour surgery, an epidural catheter for both intraoperative and postoperative pain control, a bladder catheter for drainage, a perivesical drain, and a five to six day hospital stay. Antibiotic therapy and bladder antispasmodics are required post-operatively.

Although open surgical procedures for the correction of reflux have excellent results in the hands of experienced surgeons, it is associated with a well recognized morbidity, including pain and immobilization of a lower abdominal incision, bladder spasms, hematuria, and post-operative voiding frequency in some children. In an effort to avoid open surgical intervention, widespread interest was initiated by Matouschek's clinical experience with the endoscopic injection of Teflon™(polytetrafluoroethylene) paste subureterally in 1984, as reported in Matouschek, E.: Die Behandlung des vesikorenalen Refluxes durch transueterale Einspritzung von polytetrafluoroethylenepast. *Urologe*, 20:263 (1981). With this technique, a cystoscope is inserted into the bladders, a needle is inserted through the cystoscope and placed under direct vision underneath the refluxing ureter in the submucosal space, and Teflon™ paste is injected until the gaping ureteric orifice configuration changes into a half-moon slit. The Teflon™ paste, injected endoscopically, corrects the reflux by acting as a bulking material which increases ureteral resistance. However, soon after the introduction of this treatment, a controversy regarding the use of Teflon™ paste ensued. Malizia et al. "Migration and granulomatous reaction after periurethral injection of polymer (polytetrafluoroethylene)" *JAMA*, 251:3277 (1984), showed granuloma formation and particulate migration to the brain, lungs, and lymph nodes in animal studies. Polytetrafluoroethylene migration and granuloma formation have also been reported in humans by Claes et al., "Pulmonary migration following periurethral polyetrafluoroethylene injection for urinary incontinence" *J. Urol.*, 142:821 (1989). The safety of Teflon™ for human use was questioned, and the paste was thereafter banned by the FDA.

However, there are definite advantages in treating vesicoureteral reflux endoscopically. The method is simple and can be completed in less than fifteen minutes, it has a success rate of greater than 85% with low morbidity and it can be performed in an outpatient basis, as reported by Atala et al, "Endoscopic treatment of vesicoureteral reflux with a self-detachable balloon system" *J. Urol.* 148:724 (1992). The goal of several investigators has been to find alternate implant materials which would be safe for human use.

Bovine dermal collagen preparations have been used to treat reflux endoscopically. However, only 58.5% of the patients were cured at one year follow-up, as described by Leonard et al, "Endoscopic injection of glutaraldehyde cross-linked bovine dermal collagen for correction of vesicoureteral reflux" *J. Urol.* 145:115 (1991). The collagen implant volume decreases with time, which results in high percentage of recurrence of reflux, over 90% within 3 years. The high failure rate with this substance presents a high risk to the unaware patient of developing renal damage after treatment.

A paste consisting of textured microparticles of silicone, suspended in a hydrogel, has been injected subureterally to correct reflux with an initial success rate of 91% in one European study, as reported by Buckley at al., "Endoscopic correction of vesicoureteric reflux with injectable silicone microparticles" *J. Urol.* 149: 259A (1993). However, distant particle migration has been observed in animal models, as reported by Henly et al., "Particulate silicone for use in periurethral injections: a study of local tissue effects and a search for migration" *J. Urol.* 147:376A (1992). Approximately thirty percent of the silicone particles have a diameter which is less than 100 $\mu$m. This suggests that thirty percent of the silicone particles have a potential for distant organ migration through the macrophage system. The manufacturer of this technology tried unsuccessfully to obtain FDA approval, and subsequently filed for bankruptcy.

Laparoscopic correction of reflux has been attempted in both an animal model (Atala et al, "Laparoscopic correction of vesicoureteral reflux" *J. Urol.* 150:748 (1993)) and humans (Atala, "Laparoscopic treatment of vesicoureteral reflux" *Dial Ped Urol* 14:212 (1993)) and is technically feasible. However, at least two surgeons with laparoscopic expertise are needed, the length of the procedure is much longer than with open surgery, the surgery is converted from an extraperitoneal to an intraperitoneal approach, and the cost is higher due to both increased operative time and the expense of the disposable laparoscopic equipment.

Despite the fact that over a decade has transpired since the Teflon™ controversy, little progress has been made in this area of research. The ideal substance for the endoscopic treatment of reflux should be injectable, non-antigenic, non-migratory, volume stable, and safe for human use (Atala et al, 1992).

Urinary incontinence.

Urinary Incontinence is the most common and the most intractable of all GU maladies. Urinary incontinence, or the inability to retain urine and not void urine involuntarily, is dependent on the interaction of two sets of muscles. One is the detrusor muscle, a complex of longitudinal fibers forming the external muscular coating of the bladder. The detrusor is activated by parasympathetic nerves. The second muscle is the smooth/striated muscle of the bladder sphincter. The act of voiding requires the sphincter muscle be voluntarily relaxed at the same time that the detrusor muscle of the bladder contracts. As a person ages, his ability to voluntarily control the sphincter muscle is lost in the same way that general muscle tone deteriorates with age. This can also occur when a radical event such as paraplegia "disconnects" the parasympathetic nervous system causing a loss of sphincter control. In different patients, urinary incontinence exhibits different levels of severity and is classified accordingly.

The most common incontinence, particular in the elderly, is urge incontinence. This type of incontinence is characterized by an extremely brief warning following by immediate urination. This type of incontinence is caused by a hyperactive detrusor and is usually treated with "toilet training" or medication. Reflex incontinence, on the other hand, exhibits no warning and is usually the result of an impairment of the parasympathetic nerve system such as a spinal cord injury.

Stress incontinence is most common in elderly women but can be found in women of any age. It is also commonly seen in pregnant women. This type of incontinence accounts for over half of the total number of cases. It is also found in men but at a lower incidence. Stress incontinence is characterized by urine leaking under conditions of stress such as sneezing, laughing or physical effort. There are five recognized categories of severity of stress incontinence, designated as types as 0, 1, 2a, 2b, and 3. Type 3 is the most severe and requires a diagnosis of intrinsic Sphincter Deficiency or ISD (Contemporary Urology, March 1993). There are many popular treatments including weight loss, exercise, medication and in more extreme cases, surgical intervention. The two most common surgical procedures involve either elevating the bladder neck to counteract leakage or constructing a lining from the patient's own body tissue or a prosthetic material such as PTFE to put pressure on the urethra. Another option is to use prosthetic devices such as artificial sphincters to external devices such as intravaginal balloons or penile clamps. For treatment of type 3 stress incontinence, there has been a recent trend toward injection of Teflon™ or collagen paste around the sphincter muscle in order to "beef up" the area and improve muscle tone. None of the above methods of treatment, however, are very effective for periods in excess of a year.

Overflow incontinence is caused by anatomical obstructions in the bladder or underactive detrustors. It is characterized by a distended bladder which leads to frequent urine leakage. This type of incontinence is treated acutely by catheterization and long-term by drug therapy. Enuresis or bedwetting is a problem in pediatrics and is controlled by various alarming devices and pads with sensors. Enuresis is not considered a serious problem unless it lasts beyond the age of four or five. Finally, there is true functional incontinence which occurs in patients with chronic impairment either of mobility or mental function. Such patients are usually treated by the use of diapers, incontinence pads or continuous catheterization (BBI, 1985 Report 7062).

WO 94/25080 describes the use of injectable polysaccharide-cell compositions for delivering isolated cells by injection. There is a need for improved injectable polymer-cell compositions which are biocompatible and biodegradable for delivering isolated cells by injection or implantation.

Accordingly, it is an object of the present invention to provide methods and compositions for injection of cells to form cellular tissues and cartilaginous structures.

It is a further object of the invention to provide improved compositions to form cellular tissues and cartilaginous structures including non-cellular material which will degrade and be removed to leave tissue or cartilage that is histologically and chemically the same as naturally produced tissue or cartilage.

It is another object of the present invention to provide improved methods and materials for treating vesicoureteral reflux, incontinence, and other defects which results in a natural and permanent cure to the defect.

It is a further object of the present invention to provide methods and materials for treating vesicoureteral reflux, incontinence, and other defects which is quick, simple, safe, and relatively non-invasive.

SUMMARY OF THE INVENTION

Slowly polymerizing, biocompatible, biodegradable hydrogels are provided which are useful for delivering large numbers of isolated cells into a patient to create an organ equivalent or tissue such as cartilage. The gels promote engraftment and provide three dimensional templates for new cell growth. The resulting tissue is similar in composition and histology to naturally occurring tissue. In one embodiment, cells are suspended in a polymer solution and injected directly into a site in a patient, where the polymer crosslinks to form a hydrogel matrix having cells dispersed therein. In a second embodiment, cells are suspended in a polymer solution which is poured or injected into a mold having a desired anatomical shape, then crosslinked to form a hydrogel matrix having cells dispersed therein which can be be implanted into a patient. Ultimately, the hydrogel degrades, leaving only the resulting tissue.

This method can be used for a variety of reconstructive procedures, including custom molding of cell implants to reconstruct three dimensional tissue defects, as well as implantation of tissues generally.

In another embodiment, a method of treatment of vesicoureteral reflux, incontinence and other defects is provided wherein bladder muscle cells are mixed with a liquid polymeric material, to form a cell suspension, which is injected into the area of the defect, in an amount effective to yield a tissue that corrects the defect, for example, which provides the required control over the passage of urine. In one embodiment, human bladder muscle specimens or chondrocytes are obtained and processed, the cells are mixed with the polymer, which is designed to solidify at a controlled rate when contacted with a crosslinking agent, and then the cells are injected at the desired site where they proliferate and correct the defect.

DETAILED DESCRIPTION OF THE INVENTION

Techniques of tissue engineering employing biocompatible polymer scaffolds hold promise as a means of creating alternatives to prosthetic materials currently used in craniomaxillofacial surgery, as well as formation of organ equivalents to replaced diseased, defective, or injured tissues. However, polymers used to create these scaffolds, such as polylactic acid, polyorthoesters, and polyanhydrides, are difficult to mold and hydrophobic, resulting in poor cell attachment. Moreover, all manipulations of the polymers must be performed prior to implantation of the polymeric material.

Biocompatible polymers described herein such as polysaccharides can form hydrogels which are malleable and can be used to encapsulate cells. To form a hydrogel containing the cells, a polymer solution is mixed with the cells to be implanted to form a suspension. Then, in one embodiment, the suspension is injected directly into a patient prior to crosslinking of the polymer to form the hydrogel containing the cells. The hydrogel forms over a short period of time. In a second embodiment, the suspension is injected or poured into a mold, where it crosslinks to form a hydrogel of the desired anatomical shape having cells dispersed therein which then may be implanted in a patient. The hydrogel may be produced, for example, by crosslinking a polysaccharide polymer by exposure to a monovalent cation. Other polymers capable of forming hydrogels may be used as disclosed herein, including modified alginate derivatives. In the embodiment where the polymer is crosslinked by contact with a crosslinking agent, the strength of the crosslink may be increased or reduced by adjusting the concentration of the polymer and/or crosslinking agent.

Source of Cells

Cells can be obtained directed from a donor, from cell culture of cells from a donor, or from established cell culture lines. In the preferred embodiment, cells of the same species and preferably immunological profile are obtained by biopsy, either from the patient or a close relative, which are then grown to confluence in culture using standard conditions and used as needed. If cells that are likely to elicit an immune reaction are used, such as human muscle cells from immunologically distinct individual, then the recipient can be immunosuppressed as needed, for example, using a schedule of steroids and other immunosuppressant drugs such as cyclosporine. However, in the most preferred embodiment, the cells are autologous.

In the preferred embodiments, cells are obtained directly from a donor, washed and implanted directly in combination with the polymeric material. The cells are cultured using techniques known to those skilled in the art of tissue culture. Cells obtained by biopsy are harvested and cultured, passaging as necessary to remove contaminating cells. Isolation of chondrocytes and muscle cells is demonstrated in WO 94/25080, the disclosure of which is incorporated herein.

Cell attachment and viability can be assessed using scanning electron microscopy, histology, and quantitative assessment with radioisotopes. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production.

Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted. Studies using labelled glucose as well as studies using protein assays can be performed to quantitate cell mass on the polymer scaffolds. These studies of cell mass can then be correlated with cell functional studies to determine what the appropriate cell mass is. In the case of chondrocytes, function is defined as providing appropriate structural support for the surrounding attached tissues.

This technique can be used to provide multiple cell types, including genetically altered cells, within a three-dimensional scaffolding for the efficient transfer of large number of cells and the promotion of transplant engraftment for the purpose of creating a new tissue or tissue equivalent. It can also be used for immunoprotection of cell transplants while a new tissue or tissue equivalent is growing by excluding the host immune system.

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials.

Addition of Biologically Active Materials to the hydrogel.

The polymeric matrix can be combined with humoral factors to promote cell transplantation and engraftment. For example, the polymeric matrix can be combined with angiogenic factors, antibiotics, antiinflammatories, growth factors, compounds which induce differentiation, and other factors which are known to those skilled in the art of cell culture.

For example, humoral factors could be mixed in a slow-release form with the cell-polymer suspension prior to formation of implant or transplantation. Alternatively, the hydrogel could be modified to bind humoral factors or signal recognition sequences prior to combination with isolated cell suspension.

Polymer Solutions

Polymeric materials which are capable of forming a hydrogel are utilized. The polymer is mixed with cells for implantation into the body and is permitted to crosslink to form a hydrogel matrix containing the cells either before or after implantation in the body. In one embodiment, the polymer forms a hydrogel within the body upon contact with a crosslinking agent. A hydrogel is defined as a substance formed when an organic polymer (natural or synthetic) is crosslinked via covalent, ionic, or hydrogen bonds to create a three-dimensional open-lattice structure which entraps water molecules to form a gel. Naturally occurring and synthetic hydrogel forming polymers, polymer mixtures and copolymers may be utilized as hydrogel precursors.

Examples of materials which can be used to form a hydrogel include modified alginates. Alginate is a carbohydrate polymer isolated from seaweed, which can be crosslinked to form a hydrogel by exposure to a divalent cation such as calcium, as described, for example in WO 94/25080, the disclosure of which is incorporated herein by reference. The modified alginate solution is mixed with the cells to be implanted to form a suspension. Then the suspension is injected directly into a patient prior to crosslinking of the polymer to form the hydrogel containing the cells. The suspension then forms a hydrogel over a short period of time due to the presence in vivo of physiological concentrations of calcium ions.

Alginate is ionically crosslinked in the presence of divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemical modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or $\epsilon$-caprolactone. The resulting polymer includes alginate blocks which permit ionically catalyzed gelling, and oligoester blocks which produce more rapid degradation depending on the synthetic design. Alternatively, alginate polymers may be used, wherein the ratio of mannuronic acid to guluronic acid does not produce a firm gel, which are derivatized with hydrophobic, water-labile chains, e.g., oligomers of $\epsilon$-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. As used herein, the term "modified hyaluronic acids" refers to chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., *Obstetrics & Gynecology*, 77:48–52 (1991); and Steinleitner et al., *Fertility and Sterility*, 57:305–308 (1992). Other materials which may be utilized include proteins such as fibrin, collagen and gelatin. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., *ASAID Trans.*, 38:154–157 (1992).

In general, the polymers are at least partially soluble in aqueous solutions, such as water, buffered salt solutions, or aqueous alcohol solutions. Methods for the synthesis of the other polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many polymers, such as poly(acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

In the embodiment wherein modified alginates and other anionic polymers that can form hydrogels which are malleable are used to encapsulate cells, the hydrogel is produced by cross-linking the polymer with the appropriate cation, and the strength of the hydrogel bonding increases with either increasing concentrations of cations or of polymer. Concentrations from as low as 0.001 M have been shown to cross-link alginate. Higher concentrations are limited by the toxicity of the salt.

The preferred anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

Cell Suspensions

Preferably the polymer is dissolved in an aqueous solution, preferably a 0.1 M potassium phosphate solution, at physiological pH, to a concentration forming a polymeric hydrogel, for example, for modified alginate, of between 0.5 to 2% by weight, e.g., 1%, modified alginate. The isolated cells are suspended in the polymer solution to a concentration of between 1 and 50 million cells/ml, most preferably between 10 and 20 million cells/ml.

Methods of Implantation

The techniques described herein can be used for delivery of many different cell types to achieve different tissue structures. In the preferred embodiment, the cells are mixed with the polymer solution and injected directly into a site where it is desired to implant the cells, prior to croslinking of the polymer to form the hydrogel matrix. However, the matrix may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space. For formation of cartilage, the cells are injected into the site where cartilage formation is desired. One could also apply an external mold to shape the injected solution. Additionally, by controlling the rate of polymerization, it is possible to mold the cell-hydrogel injected implant like one would mold clay. Alternatively, the mixture can be injected into a mold, the hydrogel allowed to harden, then the material implanted.

The suspension can be injected via a syringe and needle directly into a specific area wherever a bulking agent is desired, i.e., a soft tissue deformity such as that seen with areas of muscle atrophy due to congenital or acquired diseases or secondary to trauma, burns, and the like. An example of this would be the injection of the suspension in the upper torso of a patient with muscular atrophy secondary to nerve damage.

The suspension can also be injected as a bulking agent for hard tissue defects, such as bone or cartilage defects, either congenital or acquired disease states, or secondary to trauma, burns, or the like. An example of this would be an injection into the area surrounding the skull where a bony deformity exists secondary to trauma. The injunction in these instances can be made directly into the needed area with the use of a needle and syringe under local or general anesthesia.

The suspension could also be injected percutaneously by direct palpation, such as by placing a needle inside the vas deferens and occluding the same with the injected bulking substance, thus rendering the patient infertile. The suspension could also be injected through a catheter or needle with fluoroscopic, sonographic, computed tomography, magnetic resonance imaging or other type of radiologic guidance. This would allow for placement or injection of this substance either by vascular access or percutaneous access to specific organs or other tissue regions in the body, wherever a bulking agent would be required.

Further, this substance could be injected through a laparoscope or thoracoscope to any intraperitoneal or extraperitoneal or thoracic organ. For example, the suspension could be injected in the region of the gastroesophageal junction for the correcting of gastroesophageal reflux. This could be performed either with a thoracoscope injecting the substance in the esophageal portion of the gastroesophageal region, or via a laparoscope by injecting the substance in the gastric portion of the gastroesophageal region, or by a combined approach.

Vesicoureteral reflux is one of the most common congenital defects in children, affecting approximately 1% of the population. Although all patients do not require surgical treatment, it is still one of the most common procedure performed in children. Over 600 ureteral reimplants are performed yearly at Children's Hospital in Boston, Mass. This translates to an approximately saving of 3600 inpatient hospital days per year at this institution alone, if the endoscopic treatment described herein is used instead of open surgery.

In addition to its use for the endoscopic treatment of reflux, the system of injectable autologous muscle cell may also be applicable for the treatment of other medical conditions, such as urinary and rectal incontinence, dysphonia, plastic reconstruction, and wherever an injectable permanent biocompatible material is needed. Methods for using an injectable polymer for delivering isolated cells via injection are described for example in WO 94/25080.

Improved injectable biocompatible polymers are disclosed herein which are useful for example as a delivery vehicle for muscle cells or chondrocytes in the treatment of reflux and incontinence. In one exemplary embodiment, a biopsy is obtained under anesthesia from a patient with vesicoureteral reflux, the isolated cells are mixed with a polymer capable of crosslinking to form a hydrogel, and the cell-polymer solution is injected endoscopically in the sub-ureteral region to correct reflux. The time to solidification of the polymer-cell solution may be manipulated by varying the concentration of the crosslinking agent as well as the temperature at which the cells are added to the polymer. The use of autologous cells precludes an immunologic reaction. Solidification of the polymer impedes its migration until after it is degraded. The suspension can be injected through a cystoscopic needle, having direct visual access with a cystoscope to the area of interest, such as for the treatment of vesico-ureteral reflux or urinary incontinence.

In addition to the use of the cell-polymer suspension for the treatment of reflux and incontinence, the suspension can also be applied to reconstructive surgery, as well as its application anywhere in the human body where a biocompatible permanent injectable material is necessary. The suspension can be injected endoscopically, for example through a laryngoscope for injection into the vocal chords for the treatment of dysphonia, or through a hysteroscope for injection into the fallopian tubes as a method of rendering the patient infertile, or through a proctoscope, for injection of the substance in the perirectal sphincter area, thereby increasing the resistance in the sphincter area and rendering the patient continent of stool.

This technology can be used for other purposes. For example, custom-molded cell implants can be used to reconstruct three dimensional tissue defects, e.g., molds of human ears could be created and a chondrocyte-hydrogel replica could be fashioned and implanted to reconstruct a missing ear. Cells can also be transplanted in the form of a thee-dimensional structure which could be delivered via injection.

The teachings of the cited publications are indicative of the level of skill and the general knowledge of those skilled in the art. To the extent necessary, the publications are specifically incorporated herein by reference.

Modifications and variations of the compositions and methods of the present invention will be obvious to those skilled in the art from the foregoing detailed description. Such modifications and variations are intended to come within the scope of the following claims.

We claim:

1. A method for making and implanting a cell-hydrogel suspension into an animal comprising mixing dissociated cells with a solution comprising a biocompatible polymer capable of crosslinking to form a hydrogel to form a cell-polymer suspension, wherein the polymer is selected from the group consisting of (a) modified hyaluronic acids, (b) synthetic modified alginates, (c) polymers which are covalently crosslinkable by a radical reaction and (d) polymers which gel by exposure to monovalent ions;

implanting the suspension into the animal; and permitting the biocompatible polymer to crosslink and form a hydrogel matrix having the dissociated cells dispersed therein.

2. The method of claim 1 wherein the hydrogel matrix containing the dissociated cells forms before the suspension is implanted.

3. The method of claim 1 wherein the suspension of the biocompatible polymer and the dissociated cells is injected into the animal as a cell suspension; and wherein the hydrogel matrix containing the cells forms after the mixture is injected.

4. The method of claim 1 wherein the biocompatible polymer is selected from the group consisting of modified alginates and a modified hyaluronic acid.

5. The method of claim 1 wherein the hydrogel is formed by exposure of the polymer to a crosslinking agent selected from the group consisting of ions, radical initiators, and enzymes.

6. The method of claim 1 wherein the biocompatible polymer is a polysaccharide which forms a hydrogel upon exposure to a monovalent cation.

7. The method of claim 6 wherein the polymer is a polysaccharide which forms a hydrogel upon exposure to a monovalent cation.

8. The method of claim 6 wherein the monovalent cation is sodium.

9. The method of claim 5 wherein the biocompatible polymer comprises substituents capable of crosslinking by a radical reaction in the presence of a radical initiator to form a hydrogel, and wherein the biocompatible polymer is contacted with the radical initiator thereby to covalently crosslink the polymer by a radical reaction and form the hydrogel.

10. The method of claim 9 wherein the radical initiator is selected from the group consisting of a dye, ultraviolet light and visible light.

11. The method of claim 1 wherein the dissociated cells are selected from the group consisting of cells that form cartilage, cells that form bone, muscle cells, fibroblasts, and organ cells.

12. The method of claim 2 wherein the hydrogel is molded to form a specific shape prior to implantation.

13. The method of claim 3 wherein the hydrogel is molded to form a specific shape after mixing with the dissociated cells and being implanted into the animal.

14. The method of claim 1 for treating vesicoureteral reflux.

15. The method of claim 1 for treating incontinence.

16. The method of claim 1 for treating a defect in a patient within the thoracic region.

17. The method of claim 1 for treating a patient within the upper gastrointestinal tract.

* * * * *